(12) United States Patent
Lee et al.

(10) Patent No.: US 10,538,601 B2
(45) Date of Patent: Jan. 21, 2020

(54) AZASILANE-BASED MODIFIER, AND METHOD FOR PREPARING MODIFIED AND CONJUGATED DIENE-BASED POLYMER USING THE SAME

(71) Applicant: LG Chem, Ltd., Seoul (KR)

(72) Inventors: Ho Young Lee, Daejeon (KR); No Ma Kim, Daejeon (KR); Sang Mi Lee, Daejeon (KR); Da Won Chai, Daejeon (KR)

(73) Assignee: LG Chem, Ltd. (KR)

( * ) Notice: Subject to any disclaimer, the term of this patent is extended or adjusted under 35 U.S.C. 154(b) by 32 days.

(21) Appl. No.: 15/748,931

(22) PCT Filed: Feb. 24, 2017

(86) PCT No.: PCT/KR2017/002086
§ 371 (c)(1),
(2) Date: Jan. 30, 2018

(87) PCT Pub. No.: WO2017/150852
PCT Pub. Date: Sep. 8, 2017

(65) Prior Publication Data
US 2019/0002598 A1    Jan. 3, 2019

(30) Foreign Application Priority Data

Feb. 29, 2016    (KR) .......................... 10-2016-0024126

(51) Int. Cl.
| | | |
|---|---|---|
| *C08C 19/25* | (2006.01) | |
| *B60C 1/00* | (2006.01) | |
| *C08F 36/04* | (2006.01) | |
| *C08C 19/22* | (2006.01) | |
| *C08K 3/36* | (2006.01) | |
| *C08F 36/06* | (2006.01) | |
| *C08C 19/44* | (2006.01) | |
| *C08G 77/60* | (2006.01) | |
| *C07F 7/10* | (2006.01) | |
| *C08F 236/06* | (2006.01) | |
| *C08K 5/1535* | (2006.01) | |

(52) U.S. Cl.
CPC .............. *C08C 19/25* (2013.01); *B60C 1/00* (2013.01); *C07F 7/10* (2013.01); *C08C 19/22* (2013.01); *C08C 19/44* (2013.01); *C08F 36/04* (2013.01); *C08F 36/06* (2013.01); *C08F 236/06* (2013.01); *C08G 77/60* (2013.01); *C08K 3/36* (2013.01); *C08K 5/1535* (2013.01); *Y02T 10/862* (2013.01)

(58) Field of Classification Search
CPC . C07F 7/10; C08C 19/22; C08C 19/25; B60C 1/00; Y02T 10/862
See application file for complete search history.

(56) References Cited

U.S. PATENT DOCUMENTS

| | | | |
|---|---|---|---|
| 4,397,994 A | 8/1983 | Takeuchi et al. | |
| 5,281,736 A | 1/1994 | Tachikawa | |
| 5,777,144 A | 7/1998 | Rubinsztajn et al. | |
| 7,504,457 B2 | 3/2009 | Hogan et al. | |
| 7,879,945 B2 | 2/2011 | Hogan et al. | |
| 8,946,339 B2 | 2/2015 | Yoshida et al. | |
| 2004/0254301 A1 | 12/2004 | Tsukimawashi et al. | |
| 2006/0173138 A1 | 8/2006 | Hogan et al. | |
| 2009/0203844 A1* | 8/2009 | Hogan ................. | B60C 1/0016 525/105 |
| 2011/0160388 A1 | 6/2011 | Tanaka et al. | |
| 2011/0172344 A1 | 7/2011 | Yoshida et al. | |
| 2012/0322954 A1 | 12/2012 | Zupancich et al. | |
| 2013/0023624 A1 | 1/2013 | Sekikawa et al. | |
| 2015/0045474 A1 | 2/2015 | Lee et al. | |
| 2015/0342191 A1 | 12/2015 | Reddy et al. | |
| 2018/0066076 A1 | 3/2018 | Kyo et al. | |
| 2018/0162167 A1 | 6/2018 | Kyo et al. | |

FOREIGN PATENT DOCUMENTS

| | | | |
|---|---|---|---|
| CA | 1238997 A | * | 7/1988 |
| CA | 1238997 A | | 7/1988 |
| CN | 101293874 A | | 10/2008 |
| CN | 102083889 A | | 6/2011 |
| CN | 102177185 A | | 9/2011 |
| CN | 102782064 A | | 11/2012 |
| CN | 102791743 A | | 11/2012 |
| CN | 103848940 A | | 6/2014 |
| CN | 104507974 A | | 4/2015 |
| EP | 2277940 A1 | | 1/2011 |

(Continued)

OTHER PUBLICATIONS

Search report from International Application No. PCT/KR2017/002086, dated Jun. 7, 2017.
Extended European Search Report including Written Opinion for EP17760256.2 dated Jun. 27, 2018.
Chinese Search Report for Application No. 20178003004.7 dated Aug. 6, 2019, 2 pages.
Wenrun Wang, "Silane Coupler and Silicone Resin", Sichuan Science and Technology Press, Sichuan Publishing Group, Aug. 2010.

*Primary Examiner* — Nicholas E Hill
(74) *Attorney, Agent, or Firm* — Lerner, David, Littenberg, Krumholz & Mentlik, LLP

(57) ABSTRACT

The present invention provides an azasilane-based modifier of Formula 1, which may easily introduce a functional group having affinity with a filler into a conjugated diene-based polymer chain, a modified and conjugated diene-based polymer including the functional group derived from the azasilane-based modifier, a method for preparing the modified and conjugated diene-based polymer, a rubber composition including the modified and conjugated diene-based polymer, and a molded article and a tire manufactured from the rubber composition.

12 Claims, No Drawings

(56) References Cited

FOREIGN PATENT DOCUMENTS

| | | | |
|---|---:|---|---|
| EP | 2818505 | A1 | 12/2014 |
| JP | H06025264 | A | 2/1994 |
| JP | 2002020392 | A | 1/2002 |
| JP | 2008527150 | A | 7/2008 |
| JP | 2018016814 | A | 2/2018 |
| WO | 03091186 | A2 | 11/2003 |
| WO | 2009133888 | A1 | 11/2009 |
| WO | 2010044252 | A1 | 4/2010 |
| WO | 2016094186 | A1 | 6/2016 |
| WO | 2016199779 | A1 | 12/2016 |

* cited by examiner

AZASILANE-BASED MODIFIER, AND METHOD FOR PREPARING MODIFIED AND CONJUGATED DIENE-BASED POLYMER USING THE SAME

CROSS-REFERENCE TO RELATED APPLICATIONS

The present application is a national phase entry under 35 U.S.C. § 371 of International Application No. PCT/KR2017/002086, filed Feb. 24, 2017 which claims priority from Korean Patent Application No. 10-2016-0024126, filed on Feb. 29, 2016, the disclosures of which are incorporated herein by reference.

TECHNICAL FIELD

The present invention relates to an azasilane-based modifier, a modified and conjugated diene-based polymer including a functional group which is derived from the modifier, a method for preparing the modified and conjugated diene-based polymer, a rubber composition including the modified and conjugated diene-based polymer, and a molded article and a tire manufactured from the rubber composition.

BACKGROUND ART

According to the recent demand for cars having a low fuel consumption, a conjugated diene-based polymer having modulational stability represented by wet skid resistance as well as low rolling resistance, and excellent abrasion resistance and tensile properties is required as a rubber material for tires.

In order to reduce the rolling resistance of tires, there is a method of reducing hysteresis loss of vulcanized rubber, and rebound resilience at 50° C. to 80° C., tan 5, Goodrich heating, or the like is used as an evaluation index of the vulcanized rubber. That is, it is desirable to use a rubber material having high rebound resilience at the above temperature or a low tan 5 value or Goodrich heating.

Natural rubbers, polyisoprene rubbers, or polybutadiene rubbers are known as rubber materials having low hysteresis loss, but these rubbers have a limitation of low wet skid resistance. Thus, recently, conjugated diene-based (co)polymers, such as styrene-butadiene rubbers (hereinafter, referred to as "SBR") and butadiene rubbers (hereinafter, referred to as "BR"), are prepared by emulsion polymerization or solution polymerization to be used as rubbers for tires. Among these polymerization methods, the greatest advantage of the solution polymerization in comparison to the emulsion polymerization is that the vinyl structure content and the styrene content, which specify physical properties of the rubber, may be arbitrarily adjusted and its molecular weight and physical properties may be controlled by coupling or modification. Thus, the SBR prepared by the solution polymerization is widely used as a rubber material for tires because it is easy to change a structure of the finally prepared SBR or BR, and movement of chain terminals may be reduced and a coupling force with a filler such as silica and carbon black may be increased by coupling or modification of the chain terminals.

If the solution-polymerized SBR is used as the rubber material for tires, since a glass transition temperature of the rubber is increased by increasing the vinyl content in the SBR, physical properties such as running resistance and braking force, required for tires may be controlled, and fuel consumption may also be reduced by appropriately adjusting the glass transition temperature.

The solution-polymerized SBR is prepared by using an anionic polymerization initiator and is being used by coupling or modifying chain terminals of the polymer thus formed using various modifiers.

For example, U.S. Pat. No. 4,397,994 discloses a method of coupling active anions of the chain terminals of a polymer obtained by polymerizing styrene-butadiene using alkyllithium which is a monofunctional initiator in a non-polar solvent, using a binder such as a tin compound.

Meanwhile, carbon black and silica are being used as a reinforcing filler of a tire tread, wherein, in a case where the silica is used as the reinforcing filler, hysteresis loss may be low and wet skid resistance may be improved. However, since the silica having a hydrophilic surface has a low affinity with rubber in comparison to the carbon black having a hydrophobic surface, dispersibility may be poor, and, thus, there is a need to use a separate silane coupling agent to improve the dispersibility or provide coupling between the silica and the rubber.

Therefore, a method of introducing a functional group having affinity or reactivity with the silica into the terminals of rubber molecules is being performed, but its effect is insufficient.

Accordingly, the development of rubbers having high affinity with a filler such as silica is required.

DISCLOSURE OF THE INVENTION

Technical Problem

The present invention has been devised in consideration of the above-mentioned problems, and an object of the present invention is to provide a modified and conjugated diene-based polymer including a functional group which is derived from an azasilane-based modifier and is capable of showing excellent affinity with a filler in a rubber composition.

Another object of the present invention is to provide a method for preparing the modified and conjugated diene-based polymer using an azasilane-based modifier.

Further another object of the present invention is to provide a novel azasilane-based modifier.

Also, further another object of the present invention is to provide a rubber composition including the modified and conjugated diene-based polymer.

In addition, further another object of the present invention is to provide a molded article and a tire manufactured from the rubber composition.

Technical Solution

To solve the above-described tasks, according to an embodiment of the present invention, there is provided a modified and conjugated diene-based polymer including a functional group which is derived from an azasilane-based modifier represented by the following Formula 1:

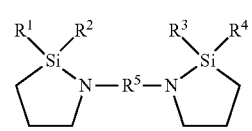

[Formula 1]

in Formula 1, $R^1$ to $R^4$ are each independently selected from the group consisting of a halogen group, an alkyl group of 1 to 6 carbon atoms and an alkoxy group of 1 to 6 carbon atoms, and $R^5$ is a divalent hydrocarbon group of 1 to 10 carbon atoms.

According to another embodiment of the present invention, there is provided a method for preparing the modified and conjugated diene-based polymer, comprising preparing an active polymer combined with an alkali metal by polymerizing conjugated diene-based monomers, or an aromatic vinyl-based monomer and a conjugated diene-based monomer in the presence of an organo-alkali metal compound in a hydrocarbon solvent; and reacting the active polymer with an azasilane-based modifier represented by Formula 1.

In addition, according to another embodiment of the present invention, there is provided an azasilane-based modifier represented by the following Formula 1:

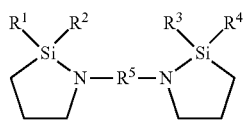

[Formula 1]

in Formula 1, $R^1$ to $R^4$ are each independently selected from the group consisting of a halogen group, an alkyl group of 1 to 6 carbon atoms and an alkoxy group of 1 to 6 carbon atoms, and $R^5$ is a divalent hydrocarbon group of 1 to 10 carbon atoms.

In addition, according to another embodiment of the present invention, there is provided a rubber composition including the modified and conjugated diene-based polymer.

Further, according to another embodiment of the present invention, there is provided a molded article and a tire manufactured from the rubber composition.

Advantageous Effects

The modified and conjugated diene-based polymer according to the present invention includes a functional group derived from an azasilane-based modifier, for example, a secondary amino group, and thus, affinity with a filler, particularly, a silica-based filler may be excellent during preparing a rubber composition.

In addition, according to the preparation method of the present invention, a functional group showing excellent affinity with a filler, for example, a secondary amino group may be easily introduced into a conjugated diene-based polymer by using the azasilane-based modifier.

Also, if the azasilane-based modifier according to the present invention is used as the modifier of a conjugated diene-based polymer, a conjugated diene-based polymer chain may be provided with a functional group showing excellent affinity with a filler, for example, a secondary amino group.

Further, since the rubber composition according to the present invention includes a modified and conjugated diene-based polymer having excellent affinity with a filler, the agglomeration of a filler in the rubber composition may be prevented, the dispersibility of the filler may be increased, and the processability of the rubber composition may be improved. As a result, the physical properties of a molded article manufactured using the rubber composition may be improved, and particularly, tensile strength, abrasion resistance, rolling resistance, and low running resistance in a tire may be improved.

BEST MODE FOR CARRYING OUT THE INVENTION

Hereinafter, the present invention will be described in more detail in order to assist the understanding of the present invention.

It will be understood that words or terms used in the specification and claims shall not be interpreted as the meaning defined in commonly used dictionaries. It will be further understood that the words or terms should be interpreted as having a meaning that is consistent with their meaning of the technical idea of the invention, based on the principle that an inventor may properly define the meaning of the words or terms to best explain the invention.

According to an embodiment of the present invention, a modified and conjugated diene-based polymer including a functional group derived from an azasilane-based modifier represented by Formula 1 below is provided.

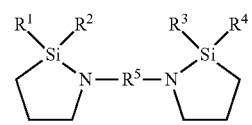

[Formula 1]

In Formula 1, $R^1$ to $R^4$ are each independently selected from the group consisting of a halogen group, an alkyl group of 1 to 6 carbon atoms and an alkoxy group of 1 to 6 carbon atoms, and $R^5$ is a divalent hydrocarbon group of 1 to 10 carbon atoms.

Particularly, the modified and conjugated diene-based polymer may include a functional group derived from the azasilane-based modifier of Formula 1, for example, a secondary amino group. More particularly, at least one of the secondary amino group may be bonded to a conjugated diene-based polymer chain.

In Formula 1, $R^1$ to $R^4$ may be each independently selected from the group consisting of a halogen group such as fluoro, chloro, and bromo; an alkyl group of 1 to 3 carbon atoms such as a methyl group, an ethyl group and a propyl group; and an alkoxy group of 1 to 3 carbon atoms such as a methoxy group, an ethoxy group and a propoxy group, more particularly, may be selected from the group consisting of a chloro group, a methyl group and a methoxy group.

In addition, in Formula 1, $R^1$ to $R^4$ may be each independently selected from the group consisting of a halogen group, an alkyl group of 1 to 3 carbon atoms and an alkoxy group of 1 to 3 carbon atoms, where one of $R^1$ and $R^2$, and one of $R^3$ and $R^4$ may be an alkyl group of 1 to 3 carbon atoms, respectively.

In addition, in Formula 1, $R^5$ may be an alkylene group of 1 to 10 carbon atoms, more particularly, an alkylene group of 2 to 8 carbon atoms, more particularly, a linear alkylene group of 3 to 6 carbon atoms such as a propylene group, a butylene group and a hexylene group.

More particularly, the azasilane-based modifier represented by Formula 1 may be a compound of Formula 2 or Formula 3 below, and one or a mixture of two thereof may be used.

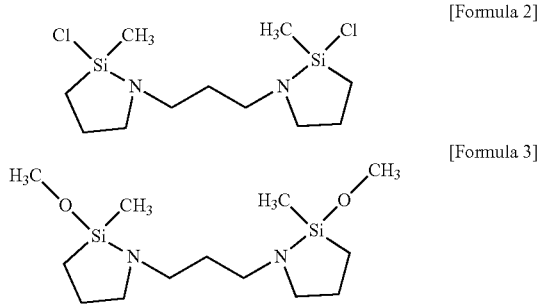

[Formula 2]

[Formula 3]

In addition, the conjugated diene-based polymer may be a homopolymer of conjugated diene-based monomers, or a copolymer of a conjugated diene-based monomer and an aromatic vinyl-based monomer.

In addition, if the modified and conjugated diene-based polymer is a copolymer, the copolymer may be a random copolymer in which structural units constituting the copolymer including a structural unit derived from the conjugated diene-based monomer and a structural unit derived from the aromatic vinyl-based monomer are arranged and combined in disorder.

Particularly, the modified and conjugated diene-based polymer may have narrow molecular weight distribution (Mw/Mn) of 1.1 to 3.0. If the molecular weight distribution of the modified and conjugated diene-based polymer is greater than 3.0 or less than 1.1, and when applying thereof to a rubber composition, it is apprehended that tensile properties and viscoelasticity may be degraded. In consideration of remarkable improving effects of the tensile properties and viscoelasticity of a polymer according to the control of the molecular weight distribution, the molecular weight distribution of the modified and conjugated diene-based polymer may particularly be from 1.3 to 3.0.

In the present invention, the molecular weight distribution of the modified and conjugated diene-based polymer may be calculated from a ratio (Mw/Mn) of a weight average molecular weight (Mw) to a number average molecular weight (Mn). In this case, the number average molecular weight (Mn) is a common average of an individual polymer molecular weight, which is obtained by measuring the molecular weights of n polymer molecules, obtaining the total of the molecular weights and dividing the total by n. The weight average molecular weight (Mw) illustrates molecular weight distribution of a polymer composition. All molecular weight average values may be expressed by gram per mol (g/mol).

In addition, in the present invention, each of the weight average molecular weight and the number average molecular weight is a polystyrene converted molecular weight analyzed by gel permeation chromatography (GPC).

In addition, the modified and conjugated diene-based polymer may satisfy the molecular weight distribution conditions and at the same time, may have a number average molecular weight (Mn) of 50,000 g/mol to 2,000,000 g/mol, more particularly, 200,000 g/mol to 800,000 g/mol. In addition, the modified and conjugated diene-based polymer may have a weight average molecular weight (Mw) of 100,000 g/mol to 4,000,000 g/mol, more particularly, 300,000 g/mol to 1,500,000 g/mol.

If the weight average molecular weight (Mw) of the modified and conjugated diene-based polymer is less than 100,000 g/mol, or the number average molecular weight (Mn) is less than 50,000 g/mol, and when the modified and conjugated diene-based polymer is applied to a rubber composition, it is apprehended that tensile properties may be degraded. In addition, if the weight average molecular weight (Mw) is greater than 4,000,000 g/mol, or the number average molecular weight (Mn) is greater than 2,000,000 g/mol, the processability of the modified and conjugated diene-based polymer may be degraded, the workability of a rubber composition may be deteriorated, difficulty is shown with mixing and kneading, and sufficient improvement of the physical properties of the rubber composition may become difficult.

More particularly, if the modified and conjugated diene-based polymer according to an embodiment of the present invention satisfies the molecular weight distribution together with the weight average molecular weight and the number average molecular weight at the same time, and when applying thereof to a rubber composition, tensile properties, viscoelasticity and processability with respect to the rubber composition may be improved in balance without being biased to any one of them.

In addition, the modified and conjugated diene-based polymer may have a vinyl content of 5 wt % or more, particularly, 10 wt % or more, more particularly, 10 wt % to 50 wt %. When the vinyl content in the range, a glass transition temperature may be controlled in an appropriate range. Accordingly, when applying the modified and conjugated diene-based polymer to tires, physical properties required for tires such as running resistance and braking force may be improved.

In this case, the vinyl content represents the amount of not 1,4-added but 1,2-added conjugated diene-based monomer based on the total amount of a conjugated diene-based polymer composed of a vinyl group-containing monomer or a conjugated diene-based monomer.

In addition, the modified and conjugated diene-based polymer according to an embodiment of the present invention has mooney viscosity (MV) of 40 to 90, particularly, 60 to 80 at 100° C. With the mooney viscosity in the range, excellent processability may be attained.

In the present invention, the mooney viscosity may be measured by using a mooney viscometer, for example, MV2000E of Monsanto Co., Ltd. using Large Rotor at a rotor speed of 2±0.02 rpm at 100° C. In this case, a specimen used was stood at room temperature (23±3° C.) for 30 minutes or more, and 27±3 g of the specimen was collected and put in a die cavity, and then, Platen was operated for measurement.

According to another embodiment of the present invention, there is provided a method for preparing the modified and conjugated diene-based polymer using the azasilane-based modifier represented by Formula 1.

The preparation method particularly comprises a step of preparing an active polymer of which at least one terminal is combined with an alkali metal by polymerizing conjugated diene-based monomers, or an aromatic vinyl-based monomer and a conjugated diene-based monomer in the presence of an organo-alkali metal compound in a hydrocarbon solvent (step 1); and a step of reacting the active polymer with an azasilane-based modifier represented by Formula 1 (step 2).

Step 1 is a step for preparing an active polymer of which at least one terminal is combined with an alkali metal, and is conducted by polymerizing conjugated diene-based monomers; or an aromatic vinyl-based monomer and a conjugated diene-based monomer in the presence of an organo-alkali metal compound in a hydrocarbon solvent.

The polymerization in step 1 may use a single type of conjugated diene-based monomer, or a conjugated diene-based monomer and an aromatic vinyl-based monomer together as monomers. That is, the polymer prepared by the preparation method according to an embodiment of the present invention may be a homopolymer of a single type of conjugated diene-based monomer; or a copolymer derived from a conjugated diene-based monomer and an aromatic vinyl-based monomer.

The conjugated diene-based monomer is not specifically limited, but may be at least one selected from the group consisting of, for example, 1,3-butadiene, 2,3-dimethyl-1,3-butadiene, piperylene, 3-butyl-1,3-octadiene, isoprene and 2-phenyl-1,3-butadiene.

If the conjugated diene-based monomer and the aromatic vinyl-based monomer are used together as the monomers, the conjugated diene-based monomer may be used in an amount such that the derived unit of the conjugated diene-based monomer is 60 wt % or more, particularly 60 wt % to 90 wt %, more particularly, 60 wt % to 85 wt % in a finally prepared modified and conjugated diene-based polymer.

The aromatic vinyl-based monomer may be, for example, at least one selected from the group consisting of styrene, α-methylstyrene, 3-methylstyrene, 4-methylstyrene, 4-propylstyrene, 1-vinylnaphthalene, 4-cyclohexylstyrene, 4-(p-methylphenyl)styrene, and 1-vinyl-5-hexylnaphthalene, without specific limitation.

If the conjugated diene-based monomer and the aromatic vinyl-based monomer are used together as the monomers, the aromatic vinyl-based monomer may be used in an amount such that an amount of the derived unit of the aromatic vinyl-based monomer in a finally prepared modified and conjugated diene-based polymer is 40 wt % or less, particularly, from 10 wt % to 40 wt %, more particularly, from 15 wt % to 40 wt %.

The hydrocarbon solvent is not specifically limited and may be, for example, at least one selected from the group consisting of n-pentane, n-hexane, n-heptane, isooctane, cyclohexane, toluene, benzene and xylene.

The organo-alkali metal compound may be used from 0.1 mmol to 1.0 mmol based on 100 g of the total monomers.

The organo-alkali metal compound may be, for example, at least one selected from the group consisting of methyllithium, ethyllithium, propyllithium, n-butyllithium, s-butyllithium, t-butyllithium, hexyllithium, n-decyllithium, t-octyllithium, phenyllithium, 1-naphthyl lithium, n-eicosyl lithium, 4-butylphenyl lithium, 4-tolyl lithium, cyclohexyl lithium, 3,5-di-n-heptylcyclohexyl lithium, 4-cyclopentyl lithium, naphthyl sodium, naphthyl potassium, lithium alkoxide, sodium alkoxide, potassium alkoxide, lithium sulfonate, sodium sulfonate, potassium sulfonate, lithium amide, sodium amide, potassium amide, and lithium isopropylamide, without specific limitation.

The polymerization of step 1 may be conducted by further adding a polar additive as needed, and the polar additive may be added in an amount of 0.001 parts by weight to 1.0 part by weight based on 100 parts by weight of the total monomers. Particularly, the addition amount may be from 0.005 parts by weight to 0.5 parts by weight, more particularly, from 0.01 parts by weight to 0.3 parts by weight based on 100 parts by weight of the total monomers.

The polar additive may be at least one selected from the group consisting of tetrahydrofuran, 2,2-di(2-tetrahydrofuryl)propane, diethyl ether, cycloamyl ether, dipropyl ether, ethylene dimethyl ether, diethyl glycol, dimethyl ether, tert-butoxy ethoxy ethane, bis(3-dimethylaminoethyl)ether, (dimethylaminoethyl) ethyl ether, trimethylamine, triethylamine, tripropylamine, and tetramethylethylenediamine.

In the preparation method according to an embodiment of the present invention, in case of copolymerizing a conjugated diene-based monomer and an aromatic vinyl-based monomer, the difference of the reaction rates therebetween may be compensated by the addition of the polar additive, thereby attaining easy formation of a random copolymer.

The polymerization of step 1 may be conducted by an adiabatic polymerization, or a polymerization at a constant temperature.

Here, the adiabatic polymerization means a polymerization method including a step of polymerization using self-generated heat of reaction without optionally applying heat after adding an organo-alkali metal compound. The polymerization at a constant temperature means a polymerization method by which the temperature of a polymer is kept constant by optionally applying or taking heat after adding an organo-alkali metal compound.

The polymerization may be conducted in a temperature range of −20° C. to 200° C., particularly, 0° C. to 150° C., more particularly, 10° C. to 120° C.

Step 2 is a step is a modification reaction step of reacting the active polymer and the azasilane-based modifier represented by Formula 1 to prepare a modified and conjugated diene-based polymer.

In this case, the azasilane-based modifier represented by Formula 1 may be the same as described above. The azasilane-based modifier represented by Formula 1 may be used in a ratio of 0.1 mol to 2.0 mol with respect to 1 mol of an organo-alkali metal compound.

The reaction of step 2 is a modification reaction for introducing a functional group into a polymer, and each reaction may be conducted in a temperature range of 0° C. to 90° C. for 1 minute to 5 hours.

The preparation method according to an embodiment of the present invention may further include at least one step of recovering and drying of solvents and unreacted monomers after step 2, if needed.

Also, according to an embodiment of the present invention, there is provided an azasilane-based modifier of Formula 1 below, which may easily introduce a secondary amino group which is a functional group having affinity with a filler into a conjugated diene-based polymer, particularly, a conjugated diene-based rubber for modification.

[Formula 1]

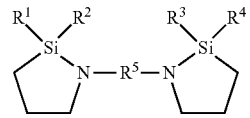

In Formula 1, $R^1$ to $R^4$ are each independently selected from the group consisting of a halogen group, an alkyl group of 1 to 6 carbon atoms and an alkoxy group of 1 to 6 carbon atoms, and $R^5$ is a divalent hydrocarbon group of 1 to 10 carbon atoms.

The azasilane-based modifier represented by Formula 1 according to an embodiment of the present invention may be a modifier for modifying the structure, properties and physical properties of a rubber, and may be readily used as a modifier of a conjugated diene-based polymer such as a butadiene-based polymer and a styrene-butadiene copolymer.

Particularly, if the azasilane-based modifier represented by Formula 1 according to an embodiment of the present invention is used as the modifier of a conjugated diene-based polymer, the modifier is combined with the conjugated diene-based polymer as a secondary amino group type. In this case, the combined secondary amino group exhibits excellent affinity with a filler, particularly, a silica-based filler in a rubber composition, and the agglomeration of the filler in the rubber composition may be prevented and dispersibility may be increased. As a result, the processability of the rubber composition including the modified and conjugated diene-based polymer may be improved, and the physical properties of a finally obtained molded article, particularly, a tire, including tensile strength, abrasion resistance, rolling resistance and low running resistance may be improved.

Further, according to another embodiment of the present invention, there is provided a rubber composition including the modified and conjugated diene-based polymer.

The rubber composition may include the modified and conjugated diene-based polymer in an amount of 0.1 wt % to 100 wt %, particularly, 10 wt % to 100 wt %, more particularly 20 wt % to 90 wt %. If the amount of the modified and conjugated diene-based polymer is less than 0.1 wt %, improving effects of abrasion resistance and crack resistance of a molded article, for example, a tire manufactured by using the rubber composition may be insignificant.

In addition, the rubber composition may further include other rubber components, if necessary, in addition to the modified and conjugated diene-based polymer, and, in this case, the rubber component may be included in an amount of 90 wt % or less based on the total amount of the rubber composition. Specifically, the rubber composition may include the rubber component in an amount of 1 part by weight to 900 parts by weight based on 100 parts by weight of the modified and conjugated diene-based copolymer.

The rubber component may be a natural rubber or a synthetic rubber, and the rubber component may be, for example, a natural rubber (NR) including cis-1,4-polyisoprene; a modified natural rubber which is obtained by modifying or purifying a common natural rubber, such as an epoxidized natural rubber (ENR), a deproteinized natural rubber (DPNR), and a hydrogenated natural rubber; and a synthetic rubber such as a styrene-butadiene copolymer (SBR), a polybutadiene (BR), a polyisoprene (IR), a butyl rubber (IIR), an ethylene-propylene copolymer, a polyisobutylene-co-isoprene, a neoprene, a poly(ethylene-co-propylene), a poly(styrene-co-butadiene), a poly(styrene-co-isoprene), a poly(styrene-co-isoprene-co-butadiene), a poly(isoprene-co-butadiene), a poly(ethylene-co-propylene-co-diene), a polysulfide rubber, an acryl rubber, a urethane rubber, a silicone rubber, an epichlorohydrin rubber, a butyl rubber, a halogenated butyl rubber, and any one or a mixture of at least two thereof may be used.

In addition, the rubber composition may include 0.1 parts by weight to 150 parts by weight of a filler based on 100 parts by weight of the modified and conjugated diene-based polymer.

The filler may particularly be a silica-based filler or a carbon black-based filler, and one or a mixture of two thereof may be used.

More particularly, the filler may be silica, more particularly, wet silica (hydrated silicate), dry silica (anhydrous silicate), calcium silicate, aluminum silicate, or colloid silica. More particularly, the filler may be wet silica which has the most significant improving effects of destruction characteristics and compatible effects of wet grip characteristics.

Meanwhile, if a silica-based filler is used as the filler, a silane coupling agent may be used together for the improvement of reinforcing and low exothermic properties.

The silane coupling agent may particularly include bis(3-triethoxysilylpropyl)tetrasulfide, bis(3-triethoxysilylpropyl)trisulfide, bis(3-triethoxysilylpropyl)disulfide, bis(2-triethoxysilylethyl)tetrasulfide, bis(3-trimethoxysilylpropyl)tetrasulfide, bis(2-trimethoxysilylethyl)tetrasulfide, 3-mercaptopropyltrimethoxysilane, 3-mercaptopropyltriethoxysilane, 2-mercaptoethyltrimethoxysilane, 2-mercaptoethyltriethoxysilane, 3-trimethoxysilylpropyl-N,N-dimethylthiocarbamoyltetrasulfide, 3-triethoxysilylpropyl-N,N-dimethylthiocarbamoyltetrasulfide, 2-triethoxysilylethyl-N,N-dimethylthiocarbamoyltetrasulfide, 3-trimethoxysilylpropylbenzothiazolyltetrasulfide, 3-triethoxysilylpropylbenzolyltetrasulfide, 3-triethoxysilylpropylmethacrylatemonosulfide, 3-trimethoxysilylpropylmethacrylatemonosulfide, bis(3-diethoxymethylsilylpropyl)tetrasulfide, 3-mercaptopropyldimethoxymethylsilane, dimethoxymethylsilylpropyl-N,N-dimethylthiocarbamoyltetrasulfide, or dimethoxymethylsilylpropylbenzothiazolyltetrasulfide, and any one or a mixture of at least two thereof may be used. More particularly, the silane coupling agent may be bis(3-triethoxysilylpropyl)polysulfide or 3-trimethoxysilylpropylbenzothiazyltetrasulfide in consideration of the improving effect of reinforcing properties.

In addition, in the rubber composition according to an embodiment of the present invention, a modified and conjugated diene-based polymer in which a functional group having high affinity with a silica-based filler is introduced into an active part is used as a rubber component, and the mixing amount of a silane coupling agent may be smaller than a common case. In particular, the silane coupling agent may be used in an amount of 1 part by weight to 20 parts by weight based on 100 parts by weight of the silica-based filler. With the amount used in the above range, effects as a coupling agent may be sufficiently exhibited, and the gelation of a rubber component may be prevented. More particularly, the silane coupling agent may be used in an amount of 5 parts by weight to 15 parts by weight based on 100 parts by weight of silica.

In addition, the rubber composition according to an embodiment of the present invention may be sulfur cross-linkable, and so may further include a vulcanizing agent.

The vulcanizing agent may be particularly a sulfur powder and may be included in an amount of 0.1 parts by weight to 10 parts by weight based on 100 parts by weight of a rubber component. With the amount used in the above range, elasticity and strength required for a vulcanized rubber composition may be secured, and at the same time, a low fuel consumption ratio may be attained.

In addition, the rubber composition according to an embodiment of the present invention may further include various additives used in a common rubber industry in addition to the above components, particularly, a vulcanization accelerator, a process oil, a plasticizer, an antiaging agent, a scorch preventing agent, a zinc white, stearic acid, a thermosetting resin, or a thermoplastic resin.

The vulcanization accelerator is not specifically limited and may particularly include thiazole-based compounds such as 2-mercaptobenzothiazole (M), dibenzothiazyldisulfide (DM), and N-cyclohexyl-2-benzothiazylsulfenamide (CZ), or guanidine-based compounds such as diphenylguanidine (DPG). The vulcanization accelerator may be included in an amount of 0.1 parts by weight to 5 parts by weight based on 100 parts by weight of the rubber component.

In addition, the process oil acts as a softener in a rubber composition and may particularly include a paraffin-based, naphthene-based, or aromatic compound. More particularly, an aromatic process oil may be used in consideration of tensile strength and abrasion resistance, and a naphthene-based or paraffin-based process oil may be used in consideration of hysteresis loss and properties at low temperature. The process oil may be included in an amount of 100 parts by weight or less based on 100 parts by weight of the rubber component. With the above-described amount, the deterioration of tensile strength and low exothermic properties (low fuel consumption ratio) of the vulcanized rubber may be prevented.

In addition, the antiaging agent may particularly include N-isopropyl-N'-phenyl-p-phenylenediamine, N-(1,3-dimethylbutyl)-N'-phenyl-p-phenylenediamine, 6-ethoxy-2,2,4-trimethyl-1,2-dihydroquinoline, or a condensate of diphenylamine and acetone at a high temperature. The antiaging agent may be used in an amount of 0.1 parts by weight to 6 parts by weight based on 100 parts by weight of the rubber component.

The rubber composition according to an embodiment of the present invention may be obtained by mulling using a mulling apparatus such as a banbury mixer, a roll, and an internal mixer according to a mixing prescription. In addition, a rubber composition having low exothermic properties and good abrasion resistance may be obtained by a vulcanization process after a molding process.

Therefore, the rubber composition may be useful to the manufacture of each member of a tire such as a tire tread, an under tread, a side wall, a carcass coating rubber, a belt coating rubber, a bead filler, a chafer, and a bead coating rubber, or to the manufacture of rubber products in various industries such as a dustproof rubber, a belt conveyor, and a hose.

Also, according to another embodiment of the present invention, there is provided a molded article and a tire manufactured using the rubber composition.

Hereinafter, the present invention will be explained in particular referring to embodiments and experimental embodiments. However, the following embodiments and experimental embodiments are only for the illustration of the present invention, and the scope of the present invention is not limited thereto.

Example 1

To a 20 L autoclave reactor, 270 g of styrene, 710 g of 1,3-butadiene, 5,000 g of n-hexane, and 1.3 g of 2,2-di(2-tetrahydrofuryl)propane as a polar additive were added, and the internal temperature of the reactor was elevated to 40° C. When the internal temperature of the reactor reached 40° C., 4 mmol of n-butyllithium was injected into the reactor, and an adiabatic reaction with heating was performed. After about 20 minutes, 20 g of 1,3-butadiene was injected for capping the terminal of SSBR with butadiene. After 5 minutes, 4 mmol of a modifier of Formula 2 below (1,3-bis(2-chloro-2-methyl-1,2-azasilolidin-1-yl)propane) was injected, and reaction was conducted for 15 minutes. Then, the polymerization reaction was quenched using ethanol, and 5 ml of a hexane solution in which 0.3 wt % of a butyrate hydroxytoluene (BHT) antioxidant was dissolved was added thereto. The polymer thus obtained was injected into hot water heated with steam, stirred to remove solvents, and roll dried to remove remaining solvents and water to prepare a modified styrene-butadiene copolymer.

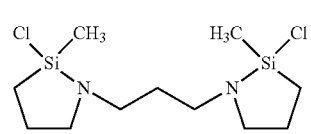

(2)

Example 2

A modified styrene-butadiene copolymer was prepared by conducting the same method described in Example 1 except for conducting modification reaction by injecting 4 mmol of a modifier of Formula 3 (1,3-(bis(2-methoxy-2-methyl-1,2-azasilolidin-1-yl)propane) instead of the modifier of Formula

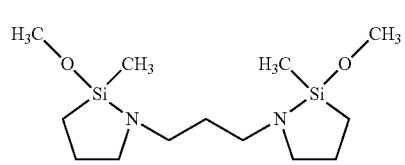

(3)

Comparative Example 1

A modified styrene-butadiene copolymer was prepared by conducting the same method described in Example 1 except for conducting modification reaction by injecting 4 mmol of tetraethoxysilane (TEOS) instead of the modifier of Formula 2.

Experimental Example 1

A weight average molecular weight (Mw), a number average molecular weight (Mn), polydispersity index (PDI), styrene derived structural unit and vinyl contents, and mooney viscosity (MV) were measured for each of the modified styrene-butadiene copolymers prepared in Examples 1 and 2 and Comparative Example 1. The results are shown in Table 1 below.

1) Analysis of Styrene Derived Structural Unit and Vinyl Contents

The styrene derived structural unit (SM) and vinyl contents in each copolymer were measured using nuclear magnetic resonance (NMR) analysis.

2) Analysis of Molecular Weights

The weight average molecular weight (Mw) and the number average molecular weight (Mn) were measured by gel permeation chromatography (GPC) analysis in conditions of 40° C. In this case, the two columns of PLgel Olexis and one column of PLgel mixed-C of Polymer Laboratories Co. Ltd. were used in combination, and newly replaced columns were all mixed bed type columns. In addition, polystyrene (PS) was used as a GPC standard material for calculating the molecular weight. Polydispersity index (PDI) was calculated from the ratio (Mw/Mn) of the weight average molecular weight (Mw) and the number average molecular weight (Mn) measured by the above method.

3) Analysis of Mooney Viscosity

The mooney viscosity of each copolymer was measured by using MV-2000 (Alpha Technologies Co., Ltd.) at 100° C. for 4 minutes after pre-heating two specimens, of which amount was 15 g or more each, for 1 minute.

TABLE 1

| | | Example 1 | Example 2 | Comparative Example 1 |
|---|---|---|---|---|
| n-butyllithium amount used (mmol) | | 0.4 | 0.4 | 0.4 |
| Modifier amount used (mmol) | | 0.4 | 0.4 | 0.4 |
| Mooney viscosity (MV) | | 67 | 77 | 98 |
| NMR | Styrene derived structural unit content (wt % based on total polymer amount) | 27.0 | 27.0 | 27.3 |
| | Vinyl content (wt % based on total polymer amount) | 43.1 | 43.1 | 42.7 |
| GPC | Mn (×10⁵ g/mol) | 13.8 | 13.8 | 14.8 |
| | Mw (×10⁵ g/mol) | 17.7 | 17.7 | 21.6 |
| | PDI (Mw/Mn) | 1.28 | 1.28 | 1.46 |

Experimental Example 2

In order to comparatively analyze the physical properties of a rubber composition including each copolymer of Examples 1 and 2 and Comparative Example 1 and a molded article manufactured therefrom, tensile properties and viscoelasticity properties were measured.

1) Preparation of Rubber Composition

Each rubber composition was prepared via a first stage mulling, a second stage mulling and a third stage mulling. In this case, the amounts used of materials excluding a modified styrene-butadiene copolymer were shown based on 100 parts by weight of the modified styrene-butadiene copolymer. In the first stage mulling, 100 parts by weight of each copolymer, 70 parts by weight of silica, 11.02 parts by weight of bis(3-triethoxysilylpropyl)tetrasulfide as a silane coupling agent, 33.75 parts by weight of a process oil (TDAE), 2.0 parts by weight of an antiaging agent (TMDQ), 2.0 parts by weight of an antioxidant, 3.0 parts by weight of zinc oxide (ZnO), 2.0 parts by weight of stearic acid, and 1.0 part by weight of wax were mixed and mulled under conditions of 80 rpm by using a banbury mixer equipped with a temperature controlling apparatus. In this case, the temperature of the mulling apparatus was controlled, and a first compound mixture was obtained at a discharge temperature of 140° C. to 150° C. In the second stage mulling, the first compound mixture was cooled to room temperature, and 1.75 parts by weight of a rubber accelerator (CZ), 1.5 parts by weight of a sulfur powder, and 2.0 parts by weight of a vulcanization accelerator were added to the mulling apparatus and mixed at a temperature of 60° C. or less to obtain a second compound mixture. Then, the second compound mixture was molded at the third stage mulling, and vulcanized at 180° C. for t90+10 minutes using a vulcanization press to prepare each vulcanized rubber.

2) Tensile Properties

The tensile properties were measured by manufacturing each specimen (thickness of 25 mm, length of 80 mm) and measuring tensile strength when broken and tensile stress when elongated by 300% (300% modulus) of each specimen according to an ASTM 412 tensile test method. Particularly, a Universal Test machine 4204 tensile tester (Instron Co., Ltd.) was used, and measurement was performed at room temperature at a rate of 50 cm/min, to obtain a tensile strength value and a tensile stress value when elongated by 300%.

3) Viscoelasticity Properties

The viscoelasticity properties were measured by using a dynamic mechanical analyzer (TA Co., Ltd.). Tan δ was measured by changing deformation at each measurement temperature (0° C. to 60° C.) with a twist mode and a frequency of 10 Hz. Payne effect (ΔG') was shown as the difference between a minimum value and a maximum value at deformation of 0.28% to 40%, and if the Payne effect decreases, it means that dispersibility of a filler is excellent. In addition, if the tan δ at a high temperature of 60° C. is low, it means that hysteresis loss is small, and low rolling resistance (fuel consumption ratio) is good.

TABLE 2

| | Example 1 | Example 2 | Comparative Example 1 |
|---|---|---|---|
| 300% modulus (Kgf/cm²) | 147 | 133 | 120 |
| Tensile strength (Kgf/cm²) | 220 | 197 | 167 |
| ΔG' | 0.50 | 0.77 | 1.20 |
| tan δ @ 0° C. | 1.067 | 1.084 | 0.942 |
| tan δ @ 60° C. | 0.084 | 0.098 | 0.124 |

Referring to the experimental results, the rubber composition including the modified styrene-butadiene copolymer of Example 1 or 2, which was modified using a modifier according to the present invention, was excellent in terms of all the properties of tensile strength, viscoelasticity and processability when compared to those of Comparative Example 1.

The invention claimed is:

1. A modified and conjugated diene-based polymer comprising a functional group which is derived from an azasilane-based modifier represented by the following Formula 1:

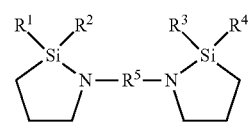

[Formula 1]

in Formula 1,
R¹ to R⁴ are each independently selected from the group consisting of a halogen group, an alkyl group of 1 to 6 carbon atoms and an alkoxy group of 1 to 6 carbon atoms, and
R⁵ is a divalent hydrocarbon group of 1 to 10 carbon atoms.

2. The modified and conjugated diene-based polymer of claim 1, wherein in Formula 1, R¹ to R⁴ are each independently selected from the group consisting of a halogen group, an alkyl group of 1 to 3 carbon atoms and an alkoxy group of 1 to 3 carbon atoms, and R⁵ is an alkylene group of 1 to 10 carbon atoms.

3. The modified and conjugated diene-based polymer of claim 1, wherein the azasilane-based modifier is a compound of the following Formula 2 or Formula 3:

[Formula 2]

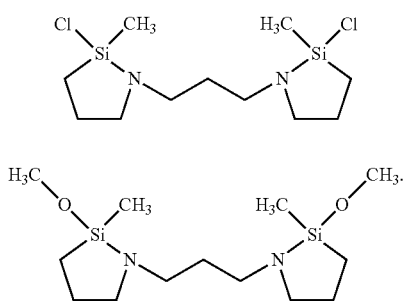

[Formula 3]

4. The modified and conjugated diene-based polymer of claim 1, wherein the modified and conjugated diene-based polymer has a number average molecular weight of 50,000 g/mol to 2,000,000 g/mol, and a weight average molecular weight of 100,000 g/mol to 4,000,000 g/mol.

5. The modified and conjugated diene-based polymer of claim 1, wherein the modified and conjugated diene-based polymer has molecular weight distribution of 1.1 to 3.0.

6. The modified and conjugated diene-based polymer of claim 1, wherein the modified and conjugated diene-based polymer has a mooney viscosity of 40 to 90 at 100° C.

7. The modified and conjugated diene-based polymer of claim 1, wherein the modified and conjugated diene-based polymer is a homopolymer of conjugated diene-based monomers, or a copolymer of a conjugated diene-based monomer and an aromatic vinyl-based monomer.

8. A method for preparing the modified and conjugated diene-based polymer of claim 1, the method comprising:
preparing an active polymer combined with an alkali metal by polymerizing conjugated diene-based monomers, or an aromatic vinyl-based monomer and a conjugated diene-based monomer in the presence of an organo-alkali metal compound in a hydrocarbon solvent; and reacting the active polymer with an azasilane-based modifier represented by the following Formula 1:

[Formula 1]

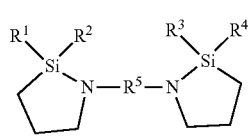

in Formula 1,
$R^1$ to $R^4$ are each independently selected from the group consisting of a halogen group, an alkyl group of 1 to 6 carbon atoms and an alkoxy group of 1 to 6 carbon atoms, and
$R^5$ is a divalent hydrocarbon group of 1 to 10 carbon atoms.

9. The method for preparing the modified and conjugated diene-based polymer of claim 8, wherein the organo-alkali metal compound is used in an amount of 0.1 mmol to 1.0 mmol based on 100 g of a total amount of monomers.

10. The method for preparing the modified and conjugated diene-based polymer of claim 8, wherein a polar additive is further added during polymerizing.

11. The method for preparing the modified and conjugated diene-based polymer of claim 10, wherein the polar additive is added in an amount of 0.001 parts by weight to 10 parts by weight based on 100 parts by weight of a total amount of monomers.

12. The method for preparing the modified and conjugated diene-based polymer of claim 8, wherein the azasilane-based modifier represented by Formula 1 is used in a ratio of 0.1 mol to 2.0 mol with respect to 1 mol of the organo-alkali metal compound.

* * * * *